United States Patent [19]

Koch

[11] Patent Number: 4,773,392

[45] Date of Patent: Sep. 27, 1988

[54] HANDHOLE FOR INFANT INCUBATOR

[75] Inventor: Robert J. Koch, Ellicott City, Md.

[73] Assignee: The BOC Group, Inc., Montvale, N.J.

[21] Appl. No.: 50,835

[22] Filed: May 13, 1987

[51] Int. Cl.[4] .............................................. A61B 19/00

[52] U.S. Cl. .................................................... 128/1 B

[58] Field of Search .............. 128/1 B, 202.12, 205.26; 220/335, 306, 260, 281, 315; 292/87, DIG. 72; 114/178

[56] References Cited

U.S. PATENT DOCUMENTS

| | | | |
|---|---|---|---|
| 2,245,487 | 6/1941 | Machin | 220/335 |
| 2,895,760 | 7/1959 | Dorsak et al. | 292/87 |
| 3,335,713 | 8/1967 | Grosholz et al. | 128/1 B |
| 4,095,640 | 6/1978 | Beckerer, Jr. | 114/178 |
| 4,296,743 | 10/1981 | Casley | 128/1 B |
| 4,343,397 | 8/1982 | Nozawa et al. | 220/335 |
| 4,693,392 | 9/1987 | Coulreras, Sr. | 220/335 |

FOREIGN PATENT DOCUMENTS

| | | | |
|---|---|---|---|
| 3609147 | 4/1987 | Fed. Rep. of Germany | 128/1 B |

*Primary Examiner*—William E. Kamm
*Assistant Examiner*—Timothy G. Philips
*Attorney, Agent, or Firm*—Roger M. Rathbun; Larry R. Cassett

[57] ABSTRACT

A handhole for use on an incubator is disclosed and which comprises only two main components, an injection molded frame attachable to the incubator by hand tightened screws and an injection molded door that is hingedly attached to the frame to pivot between open and closed positions. A bump or projection is formed on the side of the door or flange between the door and frame such that when the door is in its closed position, the bump is caught between the frame and door to cause bending of the door. By location and size of the bump, the amount of bending can be determined such that, when unlatched, the door will spring open a predetermined amount. Thus, the door's flexibility causes initial opening thereof without the need for springs or other accessories. As an added feature, the injected molded frame may include a flange for attaching a conventional wristlet thereto.

5 Claims, 2 Drawing Sheets

HANDHOLE FOR INFANT INCUBATOR

BACKGROUND OF THE INVENTION

This invention relates to infant incubators and, more particularly, to handholes for gaining access to an infant positioned within the incubator.

Handholes are conventionally used with incubators and are basically small doors that are normally closed and are opened by hospital personnel so that the personnel can insert their hands into the incubator to attend to the needs of the infant. Since the incubator provides a very closely controlled environment, both as to temperature and humidity, the handholes are used instead of opening an incubator hood, thus minimizing the disruption to that controlled environment by the admission of ambient air.

One preferred characteristic of handholes is the feature of elbow-operation, that is, for convenience, the doors of handholes are generally spring loaded such that they spring open when then latch is released. The feature is particularly advantageous since personnel utilizing incubators generally prefer to merely touch the door latch with an elbow to open that door. An example of a typical handhole door operable by an elbow is described in Grosholz et al, U.S. Pat. No. 3,335,713.

At the present time, the handholes are manufactured in numerous parts including individual coil springs and are assembled and installed on an incubator with considerable labor including extensive alignment to assure the proper orientation of the door with its frame and orientation of the latch as well as in positioning the handhole in proper position on the incubator hood. The handholes are thus relatively expensive to manufacture and install, both from the cost of individual parts and also the labor cost of assembly and installation.

SUMMARY OF THE INVENTION

The handhole of the present invention thus provides a unique construction in which only two major components are utilized, both of which are injection molded of a clear plastic composition. One component, a frame, is readily attached to the incubator by hand installed screws and thus is easily assembled and removed without special tools or the like. The frame includes a latch depending outwardly as part of its one-piece construction and includes a special flange for mounting a wristlet frame. The door likewise is a one-piece injection molded component and is hingedly connected to the frame to assume open and closed positions. In the closed position, the free end of the door is held in position by the latch.

A spring bias or effect is created by slightly bending the door when in its closed position such that when the latch is released, the inherent flexibility of the material used to construct the door causes the door to flex outwardly and thus spring to its open position by itself. Thus, the door can be opened by means of a users elbow. Preferably, the door is installed on the incubator hood at an angle with respect to the horizontal elevating the center of gravity above the hinged connection so that the weight of the door itself aids in continuing to open the door beyond the initial effect of the flexible door.

The handhole is thus elbow operated and yet is comprised of but two major injectable molded components and therefore is inexpensive to manufacture, install and remove for servicing and cleaning. In addition, because the door and frame are prealigned, the handhole can be installed without adjustment of springs or any other need to align the doors with its mating frame or latch mechanism. In effect, proper orientation is assured by manufacturing each component for preassembly of the proper dimensions. All alignment and spring action are accomplished in the molding of the two components and only final assembly to the incubator is needed.

The foregoing and other advantages and features of the present invention will become readily apparent from the following description.

BRIEF DESCRIPTION OF THE DRAWINGS

The invention is diagrammatically illustrated by way of example in the drawings appended hereto, in which.

DESCRIPTION OF THE PREFERRED EMBODIMENT

Figure 1:
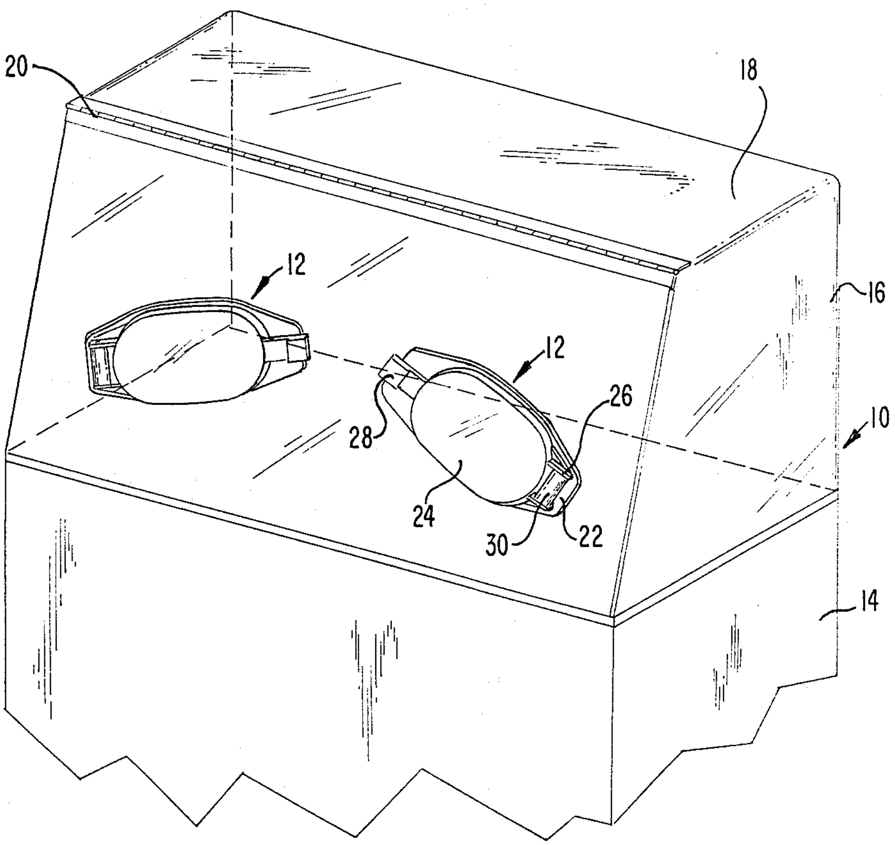
FIG. 1 is an isometric view of an incubator having installed therein, handholes constructed in accordance with the present invention.

Turning first to FIG. 1, there is shown an isometric view of an incubator 10 containing handholes 12 constructed in accordance with the present invention. In particular, incubator 10 comprises a base 14 and a hood 16 on top of the base 14 so as to enclose therein an infant compartment 18 where the infant is confined in a specially controlled environment.

That environment generally includes a heated atmosphere as well as controlled humidification. In general, hoods for such incubators are hinged, such as by piano type hinge 20 so that personnel can open the hood for complete access to the infant or for placing the infant in the incubator or removing the infant therefrom. Typical hinges are commonly also provided at the rear of the entire hood for complete opening of hood for access to the inside compartment.

As to the handhole 12 itself, it is comprised of only two basic components, a frame 22 that is secured to the hood 16 of incubator 10 and which itself has an opening, and a door 24 that is hingedly attached to the frame 22 by a hinge 26 and which pivots about the hinge 26 to both open and closed positions. Also, as shown in FIG. 1, the frame 22 includes a latch 28 that is molded integral thereto and, as will be explained, holds the door 24 in its closed position.

As shown, therefore, the handhole 12 is readily accessible to be opened by hospital or other attending personnel and which personnel can insert their hands through the handholes 12 for access to the infant, yet by minimizing the opened size, only a minimum of disruption to the internal controlled environment occurs.

The handhole 12 is, as discussed, comprised of but the two major components, that is, the frame 22 and the door 24. Each compartment is of a single piece manufactured by injection molding and preferably are of a transparent plastic such as polycarbonate which may be readily injection molded with adequate tolerances for this application. The other needed component relates to the hinge 26 and comprises a pin 30 that hingedly joins together the frame 22 and door 24.

Figure 2A:
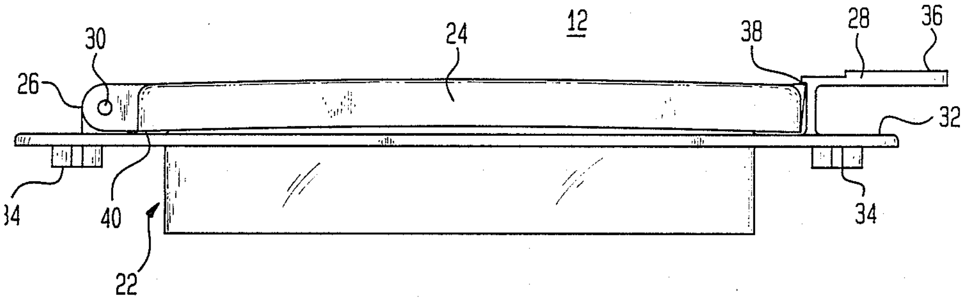
FIG. 2A is a side view of a handhole constructed in accordance with this invention.

Turning now to FIG. 2A, there is shown a side view of a handhole 12 with the door 24 in the closed position. Taking first the frame 22, the frame 22 as noted is a unitary piece of injection molded plastic and comprises a flange 32 that overlies the opening in the incubator hood when the handhole 12 is affixed to an incubator. The flange 32 includes a plurality of bosses 34 that are inserted in similarly shaped holes in the hood of the incubator and which are utilized in securing handhole 12 to an incubator. The use of bosses 34 which interfit with hand tightenable screws assure correct orientation in the installation of the handhole 12 to incubator hood 16.

The latch 28 depends outwardly from frame 22 and includes an elbow actuator 36 extending laterally outwardly forming an L shaped latch 28. By depressing the elbow actuator 36, the L shaped latch 28 flexes and moves edge 38 away from door 24 thereby releasing the door 24 as will be explained.

The door 24, as may be seen in FIG. 2A, is also a unitary piece construction of injection molded plastic. The door 24 is joined at its one end by hinge 26 to frame 22 secured thereto by pin 30, thus the door 24 is pivotable about hinge 26 to its various positions. As noted in FIG. 2A, the door 24 is held in its closed position by the overlapping relationship with latch 28 depending from flange 32.

FIG. 2A also shows the bending of door 24 in its closed position. The bending creates a spring bias toward the open position based upon the amount of such bending and the inherent flexible characteristics of the plastic material used to injection mold door 24. In order to insure that the amount of flexing is predetermined, thus the amount of bias is known, a bump 40 is injection molded into the door 24 and which bump 40 presses against flange 32 of the frame 22 when door 24 is in the closed position. By properly locating and sizing the amount of protrusion of bump 40, it is possible to predetermine the amount of bending, or bias of the door 24. That amount of protrusion is, of course, dependent upon its configuration, position and the inherent flexibility of the material used to construct door 24, and the exact dimension can readily be determined by experimentation of different locations of bump 40 and door materials. Alternate, not shown, the protrusion or bump could be injection molded on the flange 32 of frame 22.

Figure 2B:
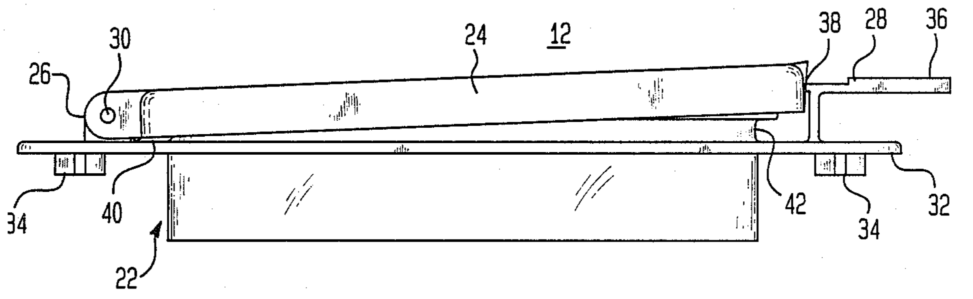
FIG. 2B is a further side view of the handhole of FIG. 2A shown with its door in the partly open position.

In FIG. 2B, there is shown a side view of the handhole 12 in which the door 24 has been released by latch 28 and has sprung open as a result of the slight bend imposed upon the door 24 in its closed position. In FIG. 2B, there can also be seen, a wristlet flange 42, also injection molded as part of the unitary piece frame 22 and which is used to attach a conventional wristlet frame that provides additionally protection to the infant's environment by forming a seal about the arms of attending personnel as they reach in to the incubator.

Returning to FIG. 1, it should be additionally noted that the bending action of door 24 is further argumented by positioning the doors 24 on incubator 10 at an angle with respect to the horizontal, thus, a center line between the center of hinge 26 and latch 28 is at an angle of approximately 5–25 degrees of the horizontal such that, the center of gravity of the door is above its pivot point. The door 24 will, after opening a slight amount by its bending bias, thereafter be aided by the force of gravity in the open direction so that the door 24 swings open to the extent necessary for personnel to gain access to the infant.

While the invention has been disclosed and described with reference to a single embodiment, it will become apparent that variations and modifications may be made therein, and it is therefore intended in the following claims to cover each such variation and modification as falls within the true spirit and scope of the invention.

I claim:

1. A handhole for attachment to an infant incubator hood comprising a one piece, injection molded plastic frame having an opening therethrough and having securing means for attachment to the incubator hood, said frame having latch means molded as a unitary piece with the frame and depending outwardly thereof, a single piece injected molded plastic door hingedly attached to said frame member and pivotable between an open and closed position with respect to said opening, said door being securable by said latch means to retain said door in its closed position, and means to impart a predetermined bending to said door when in said closed position to substantially create all of the bias required to cause said door to spring toward its open position when said latch means is unsecured.

2. A handhole as defined in claim 1 wherein said means to impart bending comprises a projection of predetermined size and location molded into said frame.

3. A handhole as defined in claim 2 wherein said injection molded plastic frame and door are both formed of polycarbonate.

4. A handhole as defined in claim 3 wherein said injection molded frame further includes a wristlet flange.

5. A handhole as defined in claim 1 wherein said means to impart bending comprises a projection of predetermined size and location molded into said door

* * * * *